United States Patent [19]

Gillespie et al.

[11] Patent Number: 4,483,920

[45] Date of Patent: Nov. 20, 1984

[54] IMMOBILIZATION OF MESSAGE RNA DIRECTLY FROM CELLS ONTO FILTER MATERIAL

[75] Inventors: David Gillespie, Glenmoore; Isadore Brodsky, Narberth; Joel Bresser, Aldan, all of Pa.

[73] Assignee: Hahnemann University, Philadelphia, Pa.

[21] Appl. No.: 378,711

[22] Filed: May 17, 1982

[51] Int. Cl.$^3$ .................. C12Q 1/68; C12P 19/34; C12N 15/00; C12N 11/12
[52] U.S. Cl. ........................ 435/6; 435/92; 435/172.2; 435/174; 435/179
[58] Field of Search .............. 435/174, 177, 179, 91, 435/172, 6

[56] References Cited

U.S. PATENT DOCUMENTS 4,302,204 11/1981 Wahl et al. .................... 435/6 X
4,358,535 11/1982 Falkow et al. .................. 435/6 X

OTHER PUBLICATIONS

Gilham, P. T., The Synthesis of Celluloses Containing Covalently Bound Nucleotides, Polynucleotides and Nucleic Acids, Biochemistry, vol. 7, No. 8, 1968 (pp. 2809-2813).
Thomas, P. S., Hybridization of Denatured RNA and Small DNA Fragments Transferred to Nitrocellulose, Proc. Nat'l. Acad. Sci. U.S.A., vol. 77, No. 9, 1980 (pp. 5201-5205).
Benton, et al., Screening λgt Recombinant Clones by Hybridization to Single Plaques in situ, Science, vol. 196, 1977 (pp. 180-182).
Thang, et al., Observations on the Activity of Enzymes after Filtration on (and through) a Nitrocellulose Membrane, Biochem. and Biophy. Res. Comm., vol. 31, No. 1, 1968 (pp. 1-8).
Poonian, et al., Covalent Attachment of Nucleic Acids to Agarose for Affinity Chromatography, Biochemistry, vol. 10, No. 3, 1971 (pp. 424-427).
Journal of the American Chemical Society, Apr. 27, 1962, pp. 1329-1338.

*Primary Examiner*—David M. Naff
*Attorney, Agent, or Firm*—Cushman, Darby & Cushman

[57] ABSTRACT

Message RNA is immobilized directly from cells onto filter material. Immobilization is carried out by solubilizing cellular components with a chaotropic salt, passing the resultant solubilized cellular components through a filter which selectively binds message RNA and baking the filter containing bound message RNA. The chaotropic salt is preferably sodium iodide, potassium iodide or sodium perchlorate. Prior to solubilizing, the cells may be washed and lysed. The bound message RNA can be hybridized to a labeled probe and the amount of message RNA measured. Prior to baking, the filter containing bound RNA may be incubated in a solution which acelylates basic protein and other molecules which might interfere with molecular hybridization.

4 Claims, No Drawings

IMMOBILIZATION OF MESSAGE RNA DIRECTLY FROM CELLS ONTO FILTER MATERIAL

BACKGROUND OF THE INVENTION (1) Field of the Invention

Tissues of patients are customarily examined for "markers" which may indicate a disease state. Marker evaluation can be an important part of a patient's initial diagnosis as well as provide a continued measurement of a patient's response to treatment and future prognosis. Conventional tissue markers include cell morphology and metabolism, the presence of certain enzymic activities or proteins or other molecules of biological import, the accumulation or disappearance of such molecules, etc. Recently, gene structure has provided a marker for certain genetic diseases (Geever et al., PNAS 78:5081-5085, 1981; Orkin et al. N. Eng.J. Med. 299:166-172, 1981, Chang and Kan PNAS 76:2886-2889, 1979; Philips et al., PNAS 77:2853-2856, 1980). However, until now it has not been possible to easily and economically measure primary gene activation, i.e., the accumulation of specific message RNA molecules (RNA transcription).

Having an appropriate "probe", usually a radiolabelled DNA molecule of known nucleotide sequence, it is possible to measure the quantity of specific message RNA species by a process called "molecular hybridization" (Gillespie, D., Methods Enzyme 12 B:641-668, 1968). Usually, the procedure involves first purifying message RNA from cells or tissues, a costly and laborious process. Molecular hybridizations utilizing purified RNA can be aided by immobilizing the RNA on a solid surface (Gilham, P. T., Biochemistry 7:2809-2813, 1968; Ponian, M. S., et al., Biochemistry 10:424-427, 1971; Wagner, A. F. et al., BBRC 45:184-189, 1971; Sheldon, R. et al., PNAS 69:417-421, 1972; Saxinger, W. C. et. al., PNAS 69:2975-2978, 1972; Noyes, B. E. and Stark, G. R., Cell 5:301-310, 1975; Alwine, J. C. et al., PNAS 74:5350-5354, 1977; Thomas, P. S., PNAS 77:5201-5205, 1980), still, RNA purification is required. Aternatively, cells can be deposited on microscope slides or a like surface and molecular hybridization can be performed upon the message RNA in the cells, a technique called "in situ molecular hybridization" (Pardue, M. L. and Gall, J. G., PNAS 64:600-604, 1969; Brahic, M. and Haase, A. T., PNAS 75:6125-6129, 1978; Angerer, L. M. and Angerer, R. C., Nuc. Ac. Res. 9:2819-2840, 1981). However, this process can be time-consuming and unreliable and is only useful when the assay can be performed upon single cells.

We have devised a process, "Direct RNA Immobilization", wherein whole cells are solubleized and passed through a filter. Most cellular constituents pass through the filter, but we have developed conditions where RNA becomes immobilized on the filter while other cell constituents which might confound molecular hybridization pass through or are inactiviated.

The process is not obvious, as evidenced by the lack of publications claiming to have developed the process. The process theoretically can be important in the diagnosis of any disease state which involves a change of RNA transcription in a tissue which can be biopsied; that is to say, virtually any disease. Practically speaking, the process is preferred over existing procedures when the existing procedures which could yield the same information are laborious, expensive or nonexistent.

We have discovered that RNA deposited on solid supports by Direct RNA Immobilization is in a suitable configuration to serve as a template for enzymatic synthesis of DNA, RNA and protein. This discovery has lead us to use Direct RNA Immobilization to develop new techniques in the field of Molecular Biology.

For example, the technique of cloning specific genes is limited by the process of screening recombinant clones for the gene of interest. When nucleic acid probes are available for the screening process, millions of clones can be screened. When no nucleic acid probes are available, under 100 clones can be screened and sometimes no screening is possible.

Using Direct RNA Immobilization we were able to develop a new cloning procedure where the screening of the clones is independent of the need for nucleic acid probes. Furthermore, the new process substantially improves the methodology for creating the initial clone bank.

(2) Description of the Prior Art

Gillespie and Spiegelman (J. Mol. Biol 12:829-842, 1965) developed a method for immobilizing purified DNA on nitrocellulose in a manner suitable for molecular hybridization. More recently Benton and Davis (Science 196:180-182, 1977), Grunstein and Hogness (PNAS 72:3961-3965, 1975), and Bresser and Gillespie (manuscript in preparation) learned how to deposit denatured DNA from dissolved viruses or cells onto nitrocellulose in a semiquantitative manner.

Several procedures have been developed over the years for the analogous immobilization of RNA (Gilham, P. T., Biochemistry 7:2809-2813, 1968; Ponian, M. S. et al., Biochemistry 10:424-427, 1971; Wagner, A. F. et al., BBRC 45:184-189, 1971; Sheldon, R. et al., PNAS 69:417-421, 1972; Saxinger, W. C. et al., PNAS 69:2975-2978, 1972; Noyes, B. E. and Stark, G. R., Cell 5:301-310, 1975; Alwine, J. C. et al., PNAS 74: 5350-5354, 1977; Thomas, P. S., PNAS 77:5201-5205, 1980). No process, save that described in this invention, demonstrates immobilization of RNA from dissolved cells. Furthermore, this invention utilizes a process and principles which are not indicated by the above referenced procedures for RNA immobilization.

SUMMARY OF THE INVENTION

We have found that cells can be dissolved in a chaotropic salt such as NaI and when such an extract is passed through a filter such as nitrocellulose membrane, the message RNA binds to the filter material. Conditions were discovered for stabilizing RNA during cell or tissue workup. Lysing procedures were developed to reduce protein-RNA and protein-nitrocellulose complexes. Modifications which reduced the viscosity of lysed cells and thereby aided filtration were discovered. Acetylation of residual protein with acetic anhydride as published by Hayashi et al. (J. Histochem. Cytochem. 26:677-679, 1978) was found to reduce background radioactivity during molecular hybridization. Washing procedures to stabilize the RNA-nitrocellulose link were worked out. Conventional conditions for specific molecular hybridization of RNA to DNA (Vogelstein, B. and Gillespie, D., BBRC 75:1127-1132, 1977) were employed.

The present method of Direct RNA Immobilization basically comprises the following steps:

(a) washing cells in inhibitors of protein synthesis and inhibitors of ribonuclease and degrading nuclear DNA with DNAase,
(b) lysing the cells by a procedure such as freeze-thaw and digestion proteins during an incubation with proteolytic enzymes,
(c) solubilizing cellular components with an aqueous solution of a chaotropic salt, e.g. saturated NaI,
(d) filtering the extract through filters which selectively bind the message RNA,
(e) washing the filters with solutions which stabilize the RNA-protein link and which remove unwanted contaminants,
(f) incubating the RNA filters in a solution which acetylates basic proteins and other molecules which might interfere with molecular hybridization,
(g) baking the RNA filters to further bond the RNA to the filter material and,
(h) performing molecular hybridization to a tagged probe, usually a radioactive, cloned DNA molecule and interpreting the hybridization result.

Certain steps (e.g. a,b,e and f) can sometimes be omitted and in certain situations, other steps may be required to achieve an acceptable result. As an alternative to step h) the enzymatic synthesis of DNA, RNA or protein can be performed, said synthesis utilizing the immobilized RNA as a template.

DESCRIPTION OF THE PREFERRED EMBODIMENTS

(a) Cell Washing

Biopsy samples of solid tissues can be effectively reduced to single cell suspension or to small clumps of cells by adding at least 2 volumes of PBSC (0.5 M NaCl, 10 mM $MgCl_2$, 0.14 M phosphate buffer, pH 6.8, 25 $\mu$g/ml cyclohexamide) and blending at low speed for 10-30 seconds in a Sorvall Omnimixer or similar contrivance. Other methods of tissue disruption that do not result in cell lysis may be equally effective.

Disrupted tissue or biopsies consisting of single cells (e.g. samples of blood, urine, sputum, lymph, etc.) or laboratory cultures of cells in PBSC are centrifuged at 1000 xg for 10 minutes to pellet the cells. Cells can be resuspended in cold PBSC and repelleted. The choice of resuspension buffer is dictated by the desire to protect intracellular RNA from degradation by "freezing" the protein synthetic machinery as with cyclohexamide and cold or by other means, such as the use of potent ribonuclease inhibitors. Isolation of specific cell types by established procedures of differential centrifugation, density gradient centrifugation or other methods can be done at this stage.

Methods of cell washing prior to cell lysis can be varied in many ways, depending on the type of tissue, manner of collection and storage, etc. In the simplest case, cyclohexamide is added to the sample and the cells are then lysed. In the more complicated situations individual cells must be obtained from solid tissues and certain cell types must be separated from the remaining tissue. The simplicity or compexity of the washing step is in no way related to the uniqueness or utility of this invention; the invention resides primarily in steps b,c,d and e, described below.

(b) Cell Lysis and Deproteinization

To washed cells is added 1 ml of 20 mM vanadyl ribonucleoside or other suitable ribonuclease inhibitor and 20 $\mu$g/ml of DNAase 1. Cells are incubated 20 minutes at 37° and 100 $\mu$g/ml of protease K or other suitable protease is added. To lyse the cells, the suspension is frozen-thawed twice in a low temperature bath such as a methanol-dry ice bath. This mixture is then held at a temperature permitting proteolysis, usually 37°. The purpose of this step is to expose RNA by (1) rupturing the cell under conditions whereby ribonucleases will not degrade said RNA and (2) removing proteins which may be bound to and "mask" RNA. Additionally, we have found that some deproteinization during cell lysis aids in the filtration and in the binding of RNA to the filter.

(c) Solublizing Cellular Components with Saturated NaI

First, a supersaturated NaI solution is made by adding 250 gms of solid NaI to 100 ml of hot water. NaI will crystallize out from the solution at room temperature but the NaI can be redissolved by heating the mixture to 75°. Then 0.813 ml of supersaturated NaI warmed to 75° is added to 1 ml of lysed, protease-treated cells. The final concentration of NaI is 100% of saturation at 25%. Any concentration over 80% of saturation at 25° can be used satisfactoraly. Concentration of under 80% of saturation at 25° can also be used in some instances, but binding and retention to membranes (see below) of RNA is suboptimal.

(d) Filtration of Dissolved Cells

The NaI solution is passed slowly through a filter under mild vacuum. The solution can also be pushed through under pressure, drawn through under centrifugal force, passed through at one gravity, etc. as long as the flow rate is not so fast as to preclude RNA binding to the filter. Nitrocellulose and glass fibers have been found to be satisfactory filter materials, cellulose acetate is unsatisfactory in that little or no RNA binds; however other suitable filter materials may be discovered in the future without adversely affecting the patent.

(e) Washing the RNA-Filter

Much of the cellular debris passes through the filter, while RNA and some DNA and presumably other molecules bind the filter material. After the NaI solution has passed through, the filter is washed with distilled water. This washing tends to remove DNA ribosomal RNA, transfer RNA and other unwanted contaminants and to help fix the message RNA to the filter. Presumably other solutions including but not limited to acids and alcohols will be equally effective in these regards.

(f) Acetylation of the RNA-Filter the RNA filter is soaked at 25° for 10 minutes in a freshly prepared solution containing 0.2 M triethanolamine and 0.25% acetaldehyde. This step acetylates basic proteins, preventing the non-specific attachment of radioactive probes to the filter during molecular hybridization. This step also inactivates filter-bound RNAase.

(g) Baking the RNA-Filter

Routinely the RNA-fulters are baked at 80° For 2 hours; however, this step can be omitted with acceptable results. For prolonged storage, water should be removed from the RNA filter, and baking is one way to accomplish this. Ordinarily, RNA filters are stored dry at room temperature.

(h) Molecular Hybridization

Any of many standard techniques can be used for molecular hybridization to DNA or RNA probes. Routinely, the filters are soaked for a few hours at hybridization temperatures in prehybridization solutions containing detergents, proteins, Ficoll, polyvinylpyrrolidone, poly(A) and DNA (Jeffreys, A. J. and Flavell, R. A., Cell 12:429–437, 1977). The most satisfactory conditions for molecular hybridization of DNA probes to RNA filters is 70–90% formamide, 0.15–0.5 M Na+, at pH 6–8 at 37–45° for several hours, because DNA-RNA hybridization is favored over DNA-DNA hybridization (Vogelstein, B. and Gillespie, D., BBRC 75:1127–1132, 1977) though any set of conditions which promotes the formation of complementary hydrogen bonds is acceptable. After hybridization, unreacted probe is removed by soaking the RNA filter in solutions similar or identical to the hybridization and/or prehybridization solutions. The extent of hybridization of the probe is a measure of corresponding RNA sequences on the filter and can be accomplished by any of several methods, including radioautography or scintillation counting. All prehybridization washing steps must be done in solutions free of nuclease activities.

The level of hybridization of a probe to the message RNA filter is directly proportional to the level of gene expression in the cells from which the message RNA was obtained. For example, if the probe is a radioactive hemoglobin gene, a high level of hybridization would reveal the presence of a large quantity of Hemoglobin-Specific message RNA on the filter and this in turn would show that the cells from which the RNA cause were actively expressing the hemoglobin gene.

(i) cDNA Synthesis on Immobilized RNA

Any several conditions for reverse transcription can be used. Typically, (Efstratiadis, A. and Villa-Komaroff, Genetic Engineering 2:15–33, 1979), we incubate RNA filters in 100 μl of 100 mM tris, pH 8.3, 10 mM Mg++, 1 μg of oligo dT, 10 mM dithiothreitol, 1 mM deoxynucleoside triphosphate (one labelled with $^3$H), 60 mM KCl and 1 unit of reverse transcriptase. The filter is incubated in this solution for 6 hours at 37°, during which time a DNA complement of the RNA template is formed and this DNA complement remains attached to the filter through the RNA template. The cDNA-RNA filter is washed several times in 30 mM tris-HCl, pH 7.5, 4 mM MgCl$_2$ and 0.5 mM 2-mercaptoethanol.

The second DNA strand is synthesized as follows (Humphries et al., Nuc. Ac. Res. 5:905–924, 1978): The filter is immersed in 50 μl of 30 mM tris-HCl, 2-pH 7.5 and incubated at 100° for 5 minutes. The filter is removed, the solution is quick-cooled to 37° and 50 μl of 30 mM tris-HCl, pH 7.5, 8 mM MgCl$_2$, 1 mM 2-mercaptoethanol, 2 mM of deoxynucleoside triphosphate and 5 units of E. coli DNA polymerase 1, Fragment A, are added. The solution is incubated for 5 hours at 22° extracted with phenol, dialyzed extensively against water, and lyophilized to dryness. To cleave the hairpin and create blunt ends the precipitate is dissolved in 25 μl of a solution containing 100 mM NaCl, 50 mM sodium acetate, pH 4.5, 1 mM zinc sulfate and 5 units of S1 endonuclease and incubated for 2 hours at 43°. The solution is extracted with phenol, dialyzed extensively against water and lyophilized to dryness.

To add oligo(dC) tails to the double-stranded DNA, the precipitate is dissolved in 100 μl of a solution containing 5 mM MgCl$_2$, 1 mM 2-mercaptoethanol, 0.6 mM dGTP and 12.5 mM Hepes-NaOH buffer, pH 7.1. 1000 units of terminal transferase is added and after incubation for 5 minutes at 37° the reaction is extracted with phenol, dialyzed extensively against water, lyophilized to dryness and stored at −20°. This preparation of tailed, double-stranded DNA copies of the immobilized message RNA is then cloned into linearized, oligo(dC)-tailed vector (Humphries et al., Nuc. Ac. Res. 5:905–924, 1978).

(j) Protein Synthesis on Immobilized RNA

Any of several conditions for protein synthesis can be used. Typically (Pelham and Jackson, Eur. J. Biochem 67:247–256, 1976), RNA filters are incubated for 60 minutes at 30° in 100 μl containing 50 μl of wheat germ extract, 30 mM KCl, 0.8 mM spermidine, 1 mM dithiothreitol, 1 mM adenosine triphosphate, 0.1 mM guanosine triphosphate, unlabeled amino acids and 5 μl of $^{35}$S methionine ($10^6$ cpm).

The invention is further illustrated by means of the following examples

EXAMPLE I

The binding of RNA to glass filters and nitrocellulose membranes

The following experiment was done to demonstrate the ability of the process to cause the binding of message RNA to filter material. Human Hela cells grown in tissue culture were labeled with radioactive uridine. Radioactive RNA was purified from these cells by conventional phenol extraction procedures. Purified radioactive RNA was made 0.5 M NaCl and passed over a column of oligo(dT)-cellulose, a column matrix which absorbs RNA bearing poly(A) tails (most message RNA) and does not absorb RNA lacking poly(A) tails (ribosomal RNA and transfer RNA). Poly(A)-containing RNA was eluted from the column with 0.01 M tris, pH 9. Poly(A)-minus RNA was passed twice again through oligo(dT)-cellulose in 0.5 M NaCl, selecting unabsorbed RNA in both cases. Poly(A)-containing RNA was made 0.5 M in NaCl, bound to oligo(dT)-cellulose and eluted in 0.01 M tris, pH 9. Over 80% of the poly(A)-containing RNA bound to a third oligo(dT)-cellulose column while under 1% of the poly(A)-minus RNA bound.

Poly(A)-containing RNA and poly(A)-minus RNA were precipitated from ethanol and dissolved in any convenient buffer, e.g., 0.01 M tris, pH 7.0. One aliquot was kept on ice and one was incubated at 37° for 60 minutes. The RNA solutions were each combined with 0.813 vols of supersaturated NaI (2.5 gm/ml H$_2$O) which had been liquified at 75°. The RNA solution was passed through glass fiber filters (Whatman GFC) or nitrocellulose membranes (Schleicher and Schuell, BA85). The filters were then washed with various solutions by suction. The results are presented in Table 1.

TABLE 1

| Filter Material and RNA | Washing Conditions | | | | | | |
|---|---|---|---|---|---|---|---|
| | No Wash | NaI | H₂O | NaI, H₂O | 18 × SSC | 18 × SSC, H₂O | H₂O 18 × SSC |
| Nitrocellulose | | | | | | | |
| poly(A)⁺RNA | * | * | 88 | 96 | 74 | 78 | 55 |
| poly(A)⁻RNA | * | * | 2 | 1 | 1 | 2 | 2 |
| Glass Fiber | | | | | | | |
| poly(A)⁺RNA | 96 | 61 | 119 | 66 | 79 | 74 | 84 |
| poly(A)⁻RNA | 101 | 101 | 7 | 10 | 29 | 5 | 5 |

Values = percent $^3$H radioactivity bound to filter
* = no determination because of quenching
18 × SSC = 2.7 M NaCl, 0.27 M Na Citrate, pH 7

Poly(A)-minus RNA bound to glass in NaI but most was removed from the filter by washings with 18×SSC (1.35 M NaCl, 0.135 M Na Citrate, pH 7) and nearly complete removal was achieved with distilled water. Binding of poly(A)-minus RNA to nitrocellulose was minimal. In contrast, poly(A)-containing RNA bound well to glass or nitrocellulose in NaI and the binding was relatively stable to several washing regimens, especially to distilled water.

It is apparent that poly(A)-containing RNA is effectively bound to the filter under the cited conditions and that most of the poly(A)-minus RNA is not. Since poly(A)-containing RNA is exclusively message RNA, as far as we know, and since most message RNA bears poly(A) tails, we conclude that the process elaborated in this example can cause the selective binding of most or all message RNA to glass or nitrocellulose filters. To the extent that some poly(A)-minus RNA is message RNA and to the extent that some poly(A)-minus RNA binds filter material we leave open the possibility that poly(A)-minus message RNA might bind filter material under the conditions we developed and we include this possibility in our patient.

We expect that similar results can be achieved with KI, NaCl₄ or other chaotropic salts and we include them in our process. Results satisfactory for some purposes might also be obtained with different temperatures of filtration of different NaI concentrations (e.g. over 50% of saturation at the temperature of filtration) and we include these changes in our process. Finally, any washing schedule is included in our process which does not remove an unreasonable amount of RNA from the filter and which does not unreasonbly interfere with subsequent steps.

EXAMPLE II

Retention of immobilized RNA under conditions of molecular hybridization, cDNA synthesis and protein synthesis $^3$H poly(A)⁺RNA from Hela cells was immobilized on nitrocellulose as described in Example I. RNA filters were then incubated under a variety of conditions and retention of the labeled RNA was measured.

RNA filters were incubated as for molecular hybridization (Jeffreys, A. J. and Flavell, R. A., Cell 12:429–439, 1977). RNA filters were prewashed for 30 minutes at 65° in 0.45 M NaCl, 0.045 M NaCit and 20 mM vanadyl ribonucleoside; then for 3 hours at 65° in the same solution containing 0.2% ficoll, 0.2% polyvinylpyrollidone, 0.2% bovine serum albumin and; then for 1 hour at 65° in the second solution containing 50 μg/ml low molecular weight salmon sperm DNA, 10 μg/ml poly(A) and 0.1% sodium dodecyl sulfate. For molecular hybridization, prewashed RNA filters were transferred to the third solution containing 25 μg/ml $^{32}$P DNA probe and incubated at 65° for 20 hours. After hybridization, RNA filters were postwashed 6 times, 5 minutes each wash at 65° with the third solution lacking poly(A). Over 60% of the immobilized RNA survived this hybridization procedure.

RNA filters were incubated for 6 hours at 37° under conditions for DNA synthesis (see part i of Description of Preferred Embodiments) without loss of immobilized RNA (91% retention).

RNA filters were incubated for 60 minutes at 30° under conditions for protein synthesis (see part j of Description of Preferred Embodiments) without loss of immobilized RNA.

EXAMPLE III

The availability of filter-bound RNA for molecular hybridization

Having demonstrated that purified message RNA (poly(A)-containing RNA) can be found to filter material (Example 1) and can be retained under conditions commonly used for molecular hybridization (Example 2), we devised an experiment to demonstrate that at least some of the RNA can be made available for molecular hybridization.

RNA was purified from human leukemic leukocytes as follows; Leukocytes, collected by leukophoresis, were washed once in phosphate buffered saline containing 25 μg/ml of cyclohexamide and once in LRSB buffer containing 25 μg/ml of cyclohexamide (LRSB=0.0001 M NaCl, 0.0025 M MgCl₂, 0.0025 M tris, pH 7.5). The leukocytes were dissolved in 0.05 M tris, pH 8, 1% sodium dodecyl sulfate, 20 mM vanadyl uridine and 25 μg/ml of cyclohexamide. To each ml of dissolved cells was added 1.3 gm of Cs₂SO₄, usually around 45° C. The solution was centrifuged at 25° and 100,000×g for 17 hours and the RNA pellet was recovered. The RNA was precipitated three times from ethanol, then poly(A)-containing RNA and poly(A)-minus RNA were purified as described in Example 1.

Solutions of poly(A)-containing RNA and poly(A)-minus RNA were combined with 0.813 volumnes of supersaturated NaI (2.5 gms NaI plus 1 ml H₂O) liquified at 75°. The resulting solutions were filtered through nitrocellulose membranes, washed with distilled water, baked at 80°, then washed with the prehybridization solutions described in Example 2. The RNA filters were then incubated at 37° for 20 hours in 50% formamide, 3×SSC (SSC=0.15 M NaCl and 0.014 M Na Citrate, pH 7), 0.05 M tris, pH 7.2, 1% diethylpyrocarbonate and 5000 cpm of radioactive ($^{32}$P) DNA probe. These conditions favor molecular hybridization. The probe was prepared by making a complementary DNA copy of the leukocyte poly(A)-containing RNA, using: reverse transcriptase enzyme from avain myeloblastosis virus, oligo(dT) primer, $^{32}P$ dCTP and other required components as published (Efstratiadis, A. and Villa-Komaroff, Genetic Engineering 2:15–33, 1979). After hybridization the filters were washed as described for post-hybridization washes in Example 2, then the amount of radioactivity on each filter was evaluated by scintillation counting.

TABLE 2

|  | Immobilized Nucleic Acid | |
| --- | --- | --- |
|  | RNA | None |
| Hybridization | 1132 | 68 |
| After RNAase | 38 | 43 |

It can be seen from Table 2 that significant hybridization occured only on the filter containing the RNA and that the molecule on the filter responsible for hybridization could be destroyed by incubation of the RNA-filter in a solution containing RNAase. On the basis of this and many other examples we conclude that the message RNA which is immobilized to the nitrocellulose filter is readily available for molecular hybridization.

Presumably, the same hybridization results could have been obtained by binding the RNA to nitrocellulose filters or other filters in other chaotropic salts as described in Example 1. RNA from other sources and/or purified by other methods will probably be equally effective (e.g. see Example 1). Other protocols for prehybridization washes, hybridization, poshybridization washes and hybrid detection will also be equivalant as long as RNA is not destroyed or otherwise made unavailable for molecular hybridization.

EXAMPLE IV

Binding to Nitrocellulose of mRNA directly from Dissolved Cells

It would obviously be advantageous to be able to directly deposit message RNA from cells onto filters in preparation for molecular hybridization, because in this circumstance the quantity of a given message RNA in a cell could be determined without the costly and laborious task of extensively purifying the RNA. Since message RNA selectively binds nitrocellulose filters in saturated NaI and since NaI dissolves cells to a great degree, it seemed resonable that conditions could be found for RNA binding from crude lysates. The following example demonstrates that this is indeed the case and reveals a few important principles which maximize the binding in a form acceptable for molecular hybridization.

Three different cell lines having different numbers of gene, dm, and consequently different amounts of dm message RNA were grown in the laboratory, then cyclohexamide was added to 25 μg/ml. Cells were released from culture flasks with 0.025% trypsin and washed with PSC (0.5 M NaCl, 0.14 M phosphate buffer, pH 6.8, 25 μg/ml cyclohexamide). One-tenth of a gram of packed cells was suspended in 0.5 ml of 0.5 M NaCl, 10 mM $MgCl_2$, 10 mM tris, pH 7.2 and made 20 mM in Vanadyl uridine and 20 μg/ml in electrophoretically pure DNAase. Cells were incubated at 37° for 30 minutes, then frozen and thawed twice in a −70° bath in the presence of 100 μg/ml of proteinase K. Lysed cells were incubated with the proteinase K for 30 minutes at 37°. To the particlly deproteinized cell lysate was added 0.813 volumes of supersaturated NaI (2.5 gms NaI/ml $H_2O$) liquified at 70°. This solution and dilutions of it in saturated NaI were passed slowly through nitrocellulose membranes, then the RNA-filters were washed with distilled water. The RNA filters were incubated for 10 minutes at 25° in freshly prepared 0.2 M triethenolamine containing 0.25% acetaladhyde to acetylate basic proteins, including RNAase, then the RNA-filters were dried at 80° for 2 hours.

The filters were washed in preparation for molecular hybridization as described in Example 2 and hybridized to a dm DNA probe using the conditions detailed in Example 2. After hybridization filters were washed to remove untreated probe (Example 2), then analyzed by scintillation counting. The results are shown in Table 3.

TABLE 3

| Cell Lines | Dilution Factor | | | | |
| --- | --- | --- | --- | --- | --- |
|  | none | 1:1 | 1:3 | 1:9 | 1:24 |
| control | 18 | 13 | 9 | 20 | 13 |
| Colo 320 | 40 | 61 | 13 | 14 | 0 |
| Colo 321 | 345 | 327 | 108 | 61 | 22 |

Values are radioactivity in cpm from triplicate samples. The control cells have 1 copy of the dm gene, Colo 320 has 75 copies of the dm gene and Colo 321 has 325 copies of the dm gene. The amount of dm message RNA is proportional to the number of dm genes.

It can be seen from Table 3 that the hybridization values are a reasonable function of the amount of dm message RNA in the cell. On the basis of this and numerous other experiments we conclude that message RNA can be deposited directly from cells onto nitrocellulose and that a suitable fraction of this message RNA, possibly all, is available for molecular hybridization. We fully expect that RNA from any cells can be so immobilized and used for molecular hybridization. Minor changes maybe necessary for adapting the process to particular cell types. For example, some cells possess high levels of ribonucleases which may degrade message RNA after cells are removed from their natural growth environment. Cyclohexamide freezes protein synthesis and minimizes message RNA degradation prior to cell disruption, but in some cases more potent protein synthesis inhibitors may be necessary. Furthermore, in some cases it may be necessary to include potent RNAase inhibitors at all steps of the process. Such inhibitors include sodium dodecyl sulfate, phenol, vanadyl ribronucleosides, diethylstilbamidine isethionate, etc. Choice of inhibitor will depend not only on the goal of RNAase inhibition but must also include absence of inhibition of essential features of the process: e.g. DNA degradation by DNAase at step b.

We also anticipate that many of the modifications of the basic process alluded to in Examples 1–3 and elsewhere in this patent application will prove to be satisfactory and we include them in our process.

It can be seen from the foregoing examples that the Direct RNA Immobilization process is capable of providing a means for evaluating the amount of a specified message RNA in a given cell sample and, consequently, is a reliable assay for the expression of specific genes in test cell samples. It should be emphasized that this is an ever-changing field and that many modifications on the basic process are obvious. We have not had the opportunity to test many of these modifications, including different inhibitors of protein synthesis, different RNAase inhibitors, different DNAases, different proteases, different methods of cell lysis, different agents for solublizing cells, different filter material, different acetylating molecules, or different conditions for molecular hybridization.

Our experiments have shown that the message RNA is attached to the filter material through the RNA poly(A) tail. As such, the heteropolymer region of said message RNA is free to participate as a template in the synthesis of complementary DNA, complementary RNA or protein.

What is claimed is:

1. A method of immobilizing message RNA from cells, comprising the steps of:
   A. Solubilizing cells containing message RNA by mixing the cells with an aqueous solution of a chaotropic salt selected from the group consisting of sodium iodide, potassium iodide, and sodium perchlorate;
   B. thereafter filtering the mixture resulting from step (A) through a filter which selectively binds and immobilizes said message RNA; and
   C. baking by heating the filter resulting from step (B) to further bond said message RNA to the filter material.

2. The method of claim 1, wherein said filter material is nitrocellulose.

3. A process for measuring quantities of a specific message RNA from cells, comprising the steps of:
   A. Solubilizing cells containing message RNA by mixing the cells with an aqueous solution of a chaotropic salt selected from the group consisting of sodium iodide, potassium iodide, and sodium perchlorate;
   B. thereafter filtering the mixture resulting from step (A) through a filter which selectively binds and immobilizes said message RNA;
   C. baking by heating filter resulting from step (B) to further bond said message RNA to the filter material; and
   D. hybridizing said bonded message RNA resulting from step (C) to a labeled probe and measuring the amount of said message RNA based on the extent of said hybridization.

4. The method of claim 3, wherein said filter material is nitrocellulose.

* * * * *